(12) United States Patent
Baker et al.

(10) Patent No.: US 10,195,299 B2
(45) Date of Patent: Feb. 5, 2019

(54) STERILIZING DEVICE AND METHOD

(71) Applicant: Baker Group, LLP, Portland, OR (US)

(72) Inventors: Michael Baker, Portland, OR (US);
John D. Russell, Portland, OR (US);
Shelby Suckow, Portland, OR (US);
Christian Terry Proch McMechan,
Victoria (CA); Mark Sasha Drlik,
Victoria (CA); Paul Charlebois,
Victoria (CA)

(73) Assignee: Baker Group, LLP, Portland, OR (US)

( * ) Notice: Subject to any disclaimer, the term of this patent is extended or adjusted under 35 U.S.C. 154(b) by 49 days.

(21) Appl. No.: 15/265,698

(22) Filed: Sep. 14, 2016

(65) Prior Publication Data

US 2017/0072077 A1    Mar. 16, 2017

Related U.S. Application Data (60) Provisional application No. 62/283,950, filed on Sep. 15, 2015.

(51) Int. Cl.
| | |
|---|---|
| *A61L 2/00* | (2006.01) |
| *G01N 23/00* | (2006.01) |
| *A61N 5/00* | (2006.01) |
| *A61L 2/10* | (2006.01) |
| *A61L 2/26* | (2006.01) |
| *A61M 25/00* | (2006.01) |
| *A61M 25/01* | (2006.01) |

(52) U.S. Cl.
CPC ............... *A61L 2/10* (2013.01); *A61L 2/26* (2013.01); *A61M 25/0017* (2013.01); *A61M 25/0111* (2013.01); *A61L 2202/11* (2013.01); *A61L 2202/24* (2013.01); *A61M 2025/0019* (2013.01)

(58) Field of Classification Search
CPC ...... A61L 2/10; A61L 2/24; A61L 2/28; H01J 37/244
USPC .............. 422/1, 24; 250/455.11, 492.1
See application file for complete search history.

(56) References Cited

U.S. PATENT DOCUMENTS

| | | | |
|---|---|---|---|
| 2004/0220519 A1 | 11/2004 | Wulfman et al. | |
| 2007/0176117 A1* | 8/2007 | Redmond | A61L 2/10 250/455.11 |

FOREIGN PATENT DOCUMENTS

| | | |
|---|---|---|
| WO | 2015095408 A1 | 6/2015 |

OTHER PUBLICATIONS

Maki, D. et al., "The risk of bloodstream infection in adults with different intravascular devices: a systematic review of 200 published prospective studies," Mayo Clinic Proceedings, vol. 81, No. 9, Sep. 2006, 26 pages.

"CDC Vitalsigns: Making Health Care Safer," CDC Website, Available Online at https://www.cdc.gov/vitalsigns/pdf/2011-03-vitalsigns.pdf, Mar. 2011, 4 pages.

(Continued)

*Primary Examiner* — Monzer R Chorbaji
(74) *Attorney, Agent, or Firm* — McCoy Russell LLP (57) ABSTRACT

Methods and systems are provided for sterilization. In one example, a device may include a body with a flexible tether and a receiving aperture having a central axis, the body forming an internal cavity, the cavity housing at least one circular battery with a central axis perpendicular to the central axis of the aperture; and a UV source positioned at an end of the receiving aperture. Various other additional features and alternative configurations are included.

19 Claims, 10 Drawing Sheets

(56) References Cited

OTHER PUBLICATIONS

The Joint Commission, "Preventing Central Line-Associated Bloodstream Infections: A Global Challenge, A Global Perspective," Available Online at https://www.jointcommission.org/assets/1/18/CLABSI_Monograph.pdf, May 2012, 152 pages.

"Summary of US Market for Infusion Therapy Devices 2013—MedSuite," ReportsnReports Website, Full Report prepared by iData Research, Available Online at http://www.reportsnreports.com/reports/596019-us-market-for-infusion-therapy-devices-2013-medsuite.html, Mar. 2013, 3 pages.

Hutchens, M. et al., "Calibration of optimal use parameters for an ultraviolet light-emitting diode in eliminating bacterial contamination on needleless connectors," Journal of Applied Microbiology, vol. 118, No. 6, Jun. 2015, Published Online Apr. 15, 2015, 9 pages.

"CSU100 Ultrasite Valve," Right Way Medical Website, Available Online at https://rightwaymed.com/product/csu100-ultrasite-valve/, Available as Early as Apr. 6, 2016, 2 pages.

"B Braun Medical—415119—Ultrasite Ag Antibacterial Luer Access Device, Needleless Connector," Stomabags Website, Available Online at http://www.stomabags.com/b-braun-medical-415119-ultrasite-ag-antibacterial-luer-access-device-needleless-connector, Available as Early as Apr. 6, 2016, 5 pages.

ISA Russian Federal Institute of Industrial Property, International Search Report Issued in Application No. PCT/US2016/051774, dated Dec. 15, 2016, WIPO, 3 pages.

ISA Russian Federal Institute of Industrial Property, Written Opinion of the International Searching Authority Issued in Application No. PCT/US2016/051774, dated Dec. 15, 2016, WIPO, 5 pages.

* cited by examiner

STERILIZING DEVICE AND METHOD

CROSS REFERENCE TO RELATED APPLICATIONS

The present application claims priority to U.S. Provisional Application Ser. No. 62/283,950, entitled "STERILIZING DEVICE AND METHOD", filed on Sep. 15, 2015, the entire contents of which are hereby incorporated by reference in their entirety for all purposes.

FIELD

The present description relates generally to sterilization of patient access sites.

BACKGROUND/SUMMARY

Patients may have one or more tubular interfacing elements placed in their body for the administration of fluids, nutrients, medications, and blood product, as well as to enable samples to be taken for diagnostic or other purposes. One example is a central venous access using a catheter or central line. As another example, dialysis catheters may be used for exchanging blood to and from a hemodialysis machine from the patient.

Sterilization of such access sites may be performed repeatedly to reduce the risk of infection and to reduce the potential for contamination. Hospital or medical staff may utilize various methods to sterilize the access sites, including alcohol wipes and/or UV exposure, as well as various other approaches.

However, the inventors herein have recognized potential issues with such approaches. For example, the tedious nature of alcohol scrubbing may result in hospital staff being incomplete or inconsistent in applying the process. Further, complete sterilization through a wiping method may be difficult and portions of the potentially contaminated interfaces may not be fully cleaned. Current UV exposure devices may be cumbersome and increase patient discomfort, or be limited in effectiveness due to improper physical couplings. Still further, available UV exposure devices may interfere with and/or damage the access sites so that the usable life of the access sites is diminished, requiring another procedure for replacement of the access site itself.

In one example disclosed in more detail herein, the issues described above may be addressed by a device including a body with a flexible tether and a receiving aperture having a central axis, the body forming a housing for a circular battery disposed with a central axis perpendicular to the central axis of the aperture, and a UV source positioned at an end of the receiving aperture.

In this way, it may be possible to provide a packaged form factor to enable easy implementation of site sterilization with improved coupling and minimal patient interference. For example, by positioning the aperture's central axis perpendicular to the central axis of the battery (or battery stack), it may be possible to locate the UV source in a way that enables efficient packaging and electrical couplings with reduced overall outside dimensions. Such a configuration may even be tethered to the patient via the access site line itself.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIGS. 1-9 are drawn to scale, although other relative dimensions may be used, if desired.

DETAILED DESCRIPTION

The following description relates to systems and methods for sterilizing a patient access site. The patient may be a human patient or an animal patient.

Figure 1:
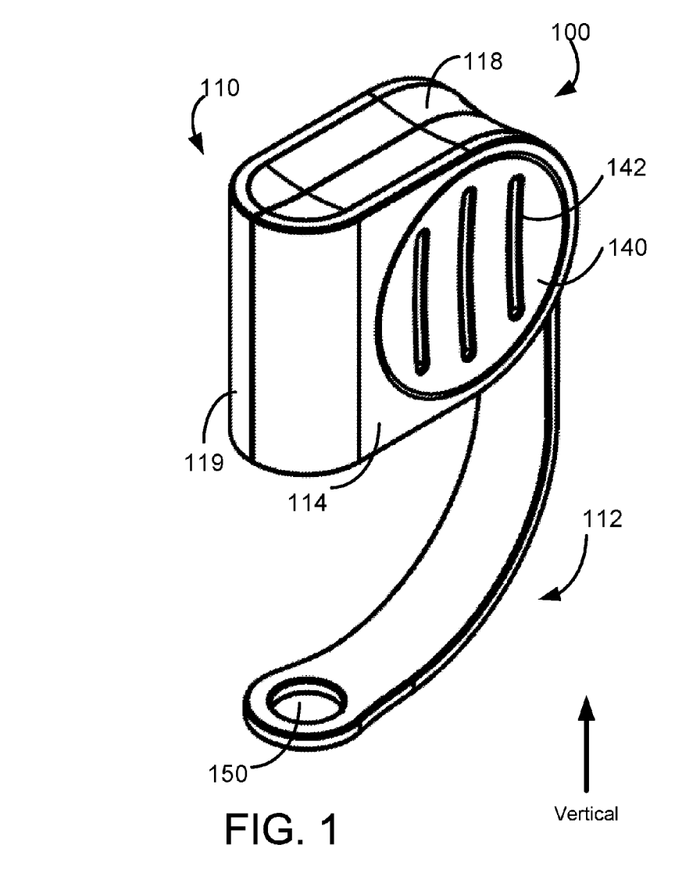
FIGS. 1-9 show a first example device with and without a port coupled therein.
Figure 2:
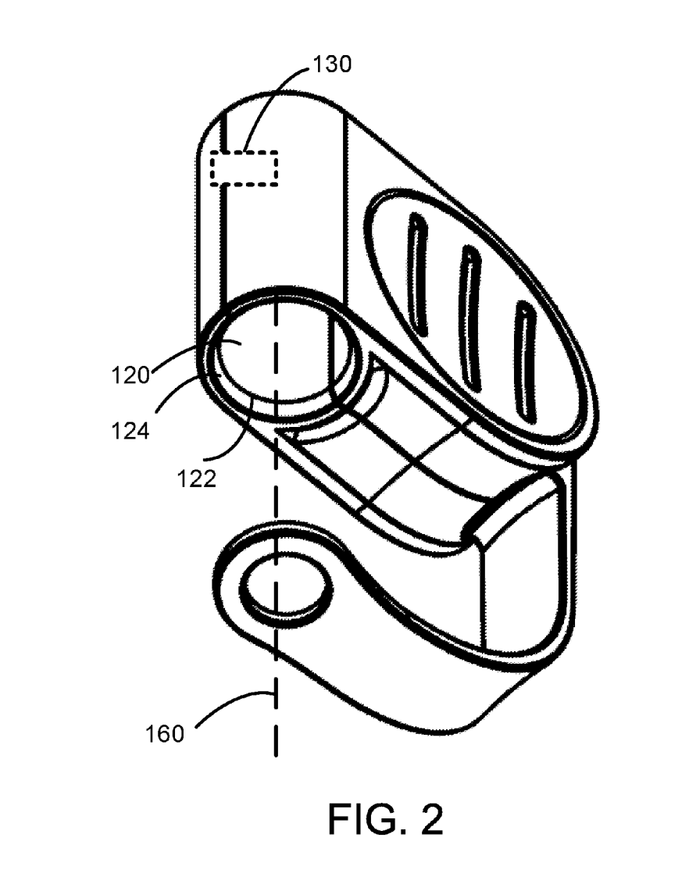
Figure 3:
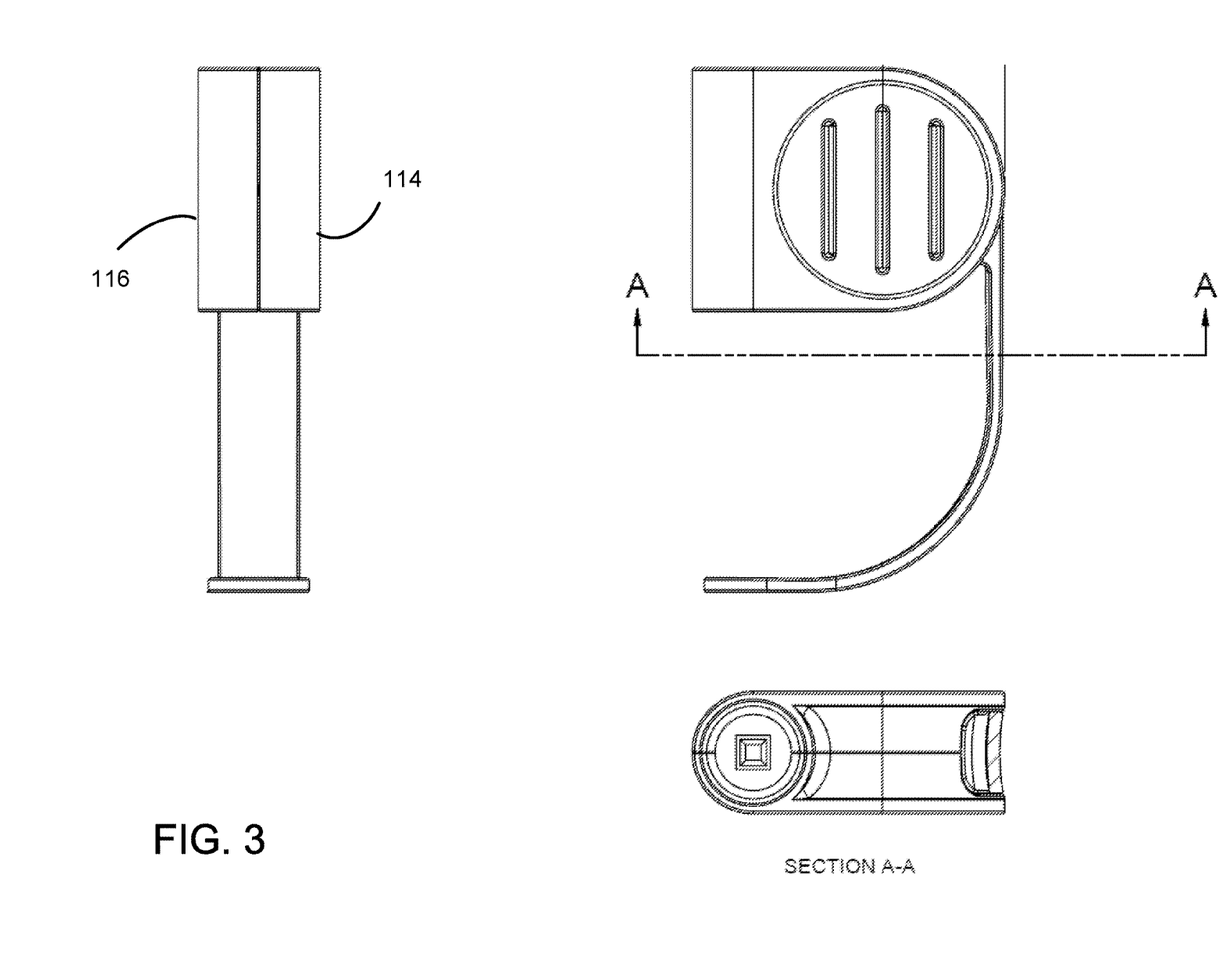

A first example device 100 is illustrated in FIGS. 1-11. Specifically, FIGS. 1-3 show a device 100 that may include a body 110 with a tether 112. In one example, the body may be formed of a clam-shell of plastic, such as PVC, PET, PETE, and/or another plastic and/or combinations thereof via exterior walls. The plastic body may be considered to form a hard surface (and thus non-flexible as compared with flexible components described herein).

In the illustrated example, the exterior walls may include a first planar wall 114 and an opposite or opposing planar wall 116. The opposing planar wall may be parallel or substantially parallel to the first planar wall 114. In some examples, a curved concave edge wall 118 may extend along a top of the body, wrapping down along a side of the bottom, and then continuing uninterrupted to wrap around and long the bottom of the body to the aperture 120. It should be appreciated that one or more sections may be used to form the edge wall. Further, in some examples, the edge wall may be more or less curved, and in some examples, one or more features may extend from the edge wall.

The body may have an aperture 120 for receiving a port, such as a catheter port, needleless injector port, etc. The aperture may form a cylindrical receiving portion with cylindrical walls positioned inside (e.g., wholly within) the body 110. The body 110 may form an internal cavity or housing where the cylindrical receiving portion with its cylindrical walls are positioned inside (e.g., wholly within) the cavity where an exterior circular opening 122 is the only opening with a void space therein in the exterior walls of the body 110.

A front convex exterior wall 119 may be formed opposite the back side of the body extending completely and fully uninterrupted from the top of the body to the bottom of the body and the aperture 120. The walls may form a completely continuous body exterior except for the aperture 120. However, in some examples, various additional openings may be provided.

In some examples, a window 130 may be provided. The window may be formed of a UV-activated material to generate visible light illuminated to indicate operation of the device to a user, patient, external detector, etc. The window may be formed of a continuous material so that there is no fluidic communication between exterior and interiors of the body through the fixed window. Further, the window is shown positioned on wall 119, although it may be positioned in other locations as well. Likewise, additional windows may also be provided, formed and structured similarly as window 130, to provide multiple indications of device operation to users or other detectors positioned at different locations. For example, a patient's clothing or body may obscure one window, but another window positioned in a different location of the device (e.g., an opposite wall) may thus still be visible.

Each of or only one of walls 114 and 116 may include a gripping region. For example, as illustrated, a circular concave gripping region 140 may be recessed into body 110 and not protruding outside an outer periphery of the body in a direction perpendicular to wall 114. In other examples, the gripping region may be raised or form an extended ridge or slot for gripping. Such configurations are within the scope of the disclosure.

The gripping region 140 may include one or more recesses and/or protrusions 142. In one example, the recesses and/or protrusions 142 may enable connection to another similar device 110 so that multiple devices may be stacked together with respective side walls in face-sharing contact and respective recesses mating with protrusions in a snap-fit connection to removeably couple two or more devices together. In the example shown in the figures, three recesses/protrusions 142 are shown, each being elongate and vertically positioned with respect to the top and bottom of the device with vertical shown in the figures merely to enable description of the components, as the device in use may be positioned in any orientation (e.g., it likely may be upside down as it hangs on a patients line). Of the three recesses/protrusions 142, a central line may be a longest, with two side lines symmetrically positioned, each being shorter in length. Any number of recesses and protrusions may be integrated. In one example, wall 114 has protrusions 142, while wall 166 has recesses (not shown but physically positioned symmetric and opposite the protrusions 142).

Tether 112 may be comprised of a flexible material to enable easy manipulation and maneuverability of the device even if one end of the tether is fixed, for example to a line inserted into the body via a retaining slot or 150. The retaining slot may include, in some examples, a slit for easy removal and insertion. As illustrated, in some examples, the tether extends initially parallel to a central axis 160 of the aperture 120. In some examples, tether 112 may be bent or flexed to align hole 150 with aperture 120. Although shown as integrally coupled to body 110, in some examples, the tether may be selectively removed from the body to allow replacement of one of the tether or the body. Further in some examples, different lengths of tethers and material flexibility for the tether may be utilized.

Aperture 120 may include a flexible seal 124, which may be annularly shaped and extending completely around and forming opening 122. The seal may be angled inwardly into the cylindrical receiving cavity.

In one example, the body may be In this configuration the top edge wall forms a first side of the U-shape with the bottom edge wall forming the opposing side of the U-shape.

Figure 4:
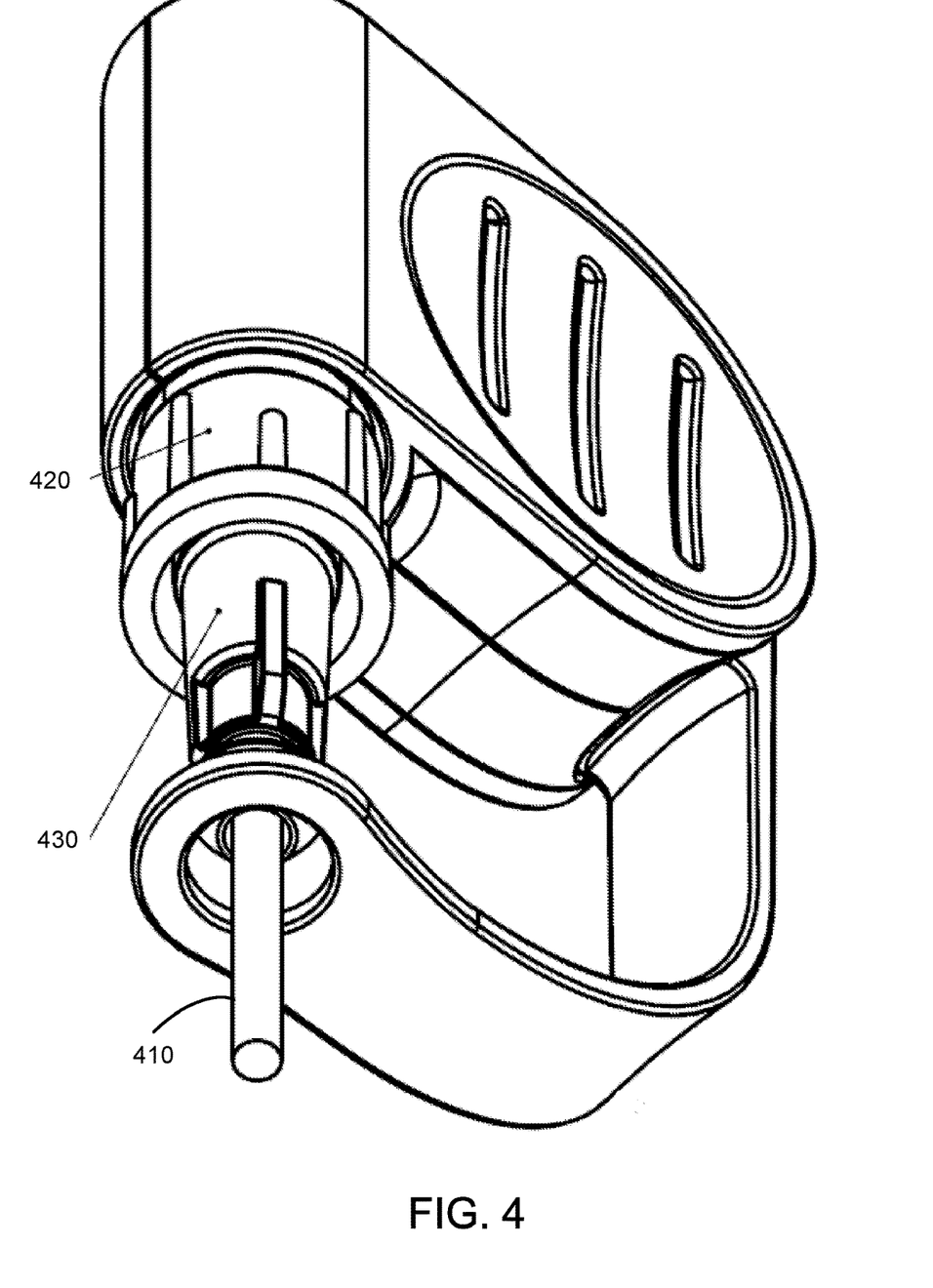
Figure 5:
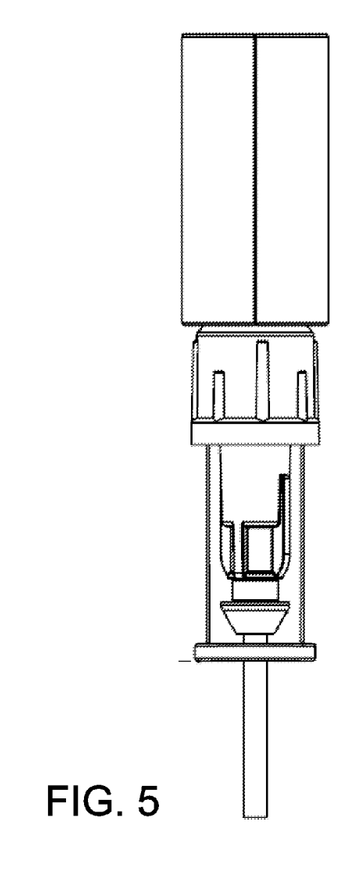
Figure 6:
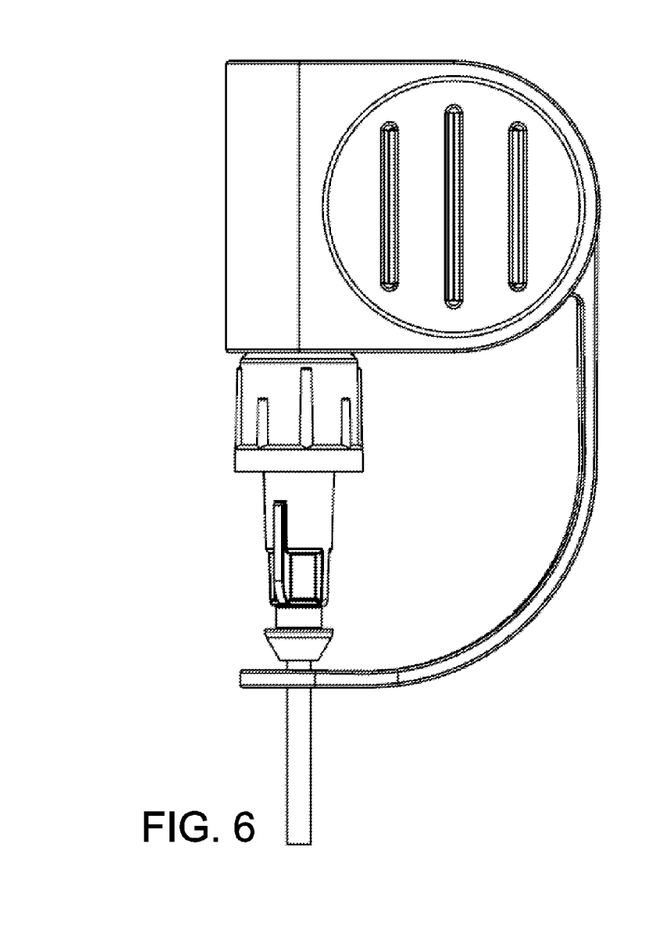
Figure 7:
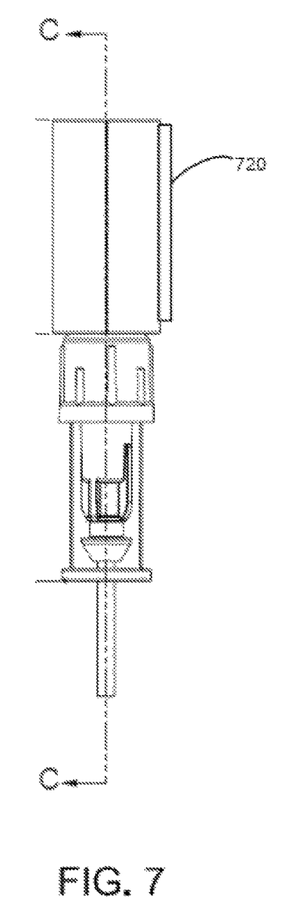
Figure 8:
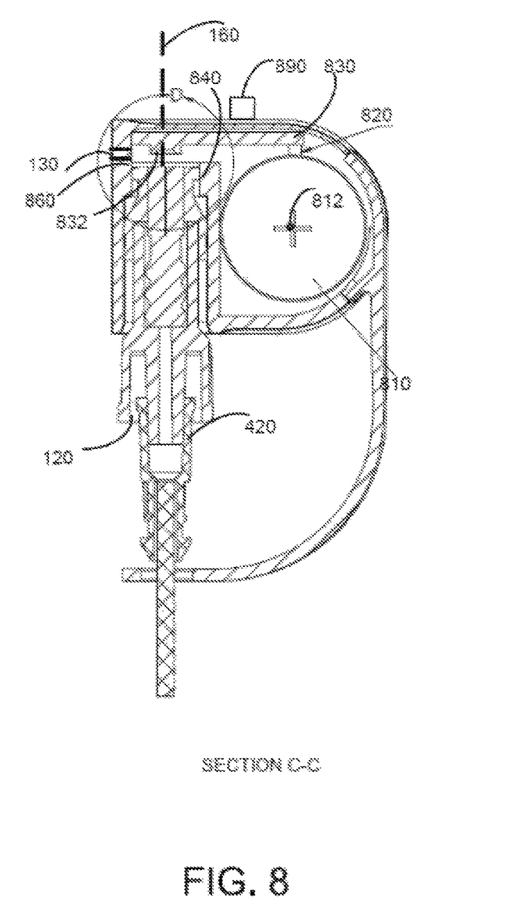

FIGS. 4-6 show the device 100 coupled with a tube or line 410. In this example, a needle-free injection port (female/male luer) 420 is illustrated. The top of the needle free injection port is positioned within device 100 to be sterilized by UV light. In one example, the port may be secured and recessed into the body by a threaded connection with the body. Additionally, a female-luer to catheter transition 430 is shown attached to the needle-free injection port via a threaded connection and luer, also slideably coupled to the tether. In some examples, additional or alternative connectors or locks may be used, alternatively, or in combination, with the threads to position and/or secure the port in the body FIGS. 7 and 8 further illustrate the device 100 with needle free injection port 420 positioned in aperture 120. FIG. 8 shows a cross section from FIG. 7 along line C-C illustrating internal components of the device.

As illustrated, within body 110, an energy storage device 810 is disposed. In the illustrated example, energy storage device 810 is shown as a stack of circular batteries electrically coupled via an electrical connection 820 to circuit board 830. Board 830 may be fixedly mounted to an internal wall of the body, such as in this example, a top internal surface of the body. In one example, the board is mounted directly to a top internal wall of the body. Although in other examples the board may be positioned along one of the other wall surfaces or integrated along the walls forming aperture 120. Components of board 830 are described below in regards to FIG. 8 and in regards to FIG. 11.

Additionally, the energy storage device 810 may have a central axis in and out of the page at 812 that is perpendicular to the top surface as well as the central axis of the aperture. The energy storage device 810 may be positioned such that the curved walls of the example batteries are positioned in a bottom U portion of the U-shaped body, with the curvature of the bottom U portion matching a curvature of the example batteries.

Internal walls 840 of the cavity may divide the energy storage device 810 from contacting or interacting with the void of the cavity where the port may be positioned. The energy-storage facing walls of walls 840 may create a cavity for the energy storage device. For example, the energy-storage facing walls may secure energy storage device 810 in place in one example, pressing it against connection 820 in a spring-loaded fashion to maintain electrical connections. In some examples, additional structure, including recesses, protrusions or slots may be used to secure the energy storage device in position.

In the illustrated example, board 830 may include a surface mounted LED 832 directly facing an abutting end of the aperture or cavity. The LED may have its central axis aligned with axis 160 in one example. In another example, the LED may be operatively connected to the board such that the LED is aligned with the receiving aperture without being surface mounted to the board. The LED 832 may be a UV LED adapted to UV sterilize the needle-free port. Further, operation of LED 832 are described below.

Window 130, described above, is shown positioned between LED and the abutment 860 which extends across and encloses the receiving cavity portion or aperture. The abutment 860 may be formed of a clear plastic in one example to enable transmission of the UV energy from the LED to the inserted port. Window 130 may be utilized, in some examples, to view operating status of the LED.

In a further example, an additional status LED, such as LED 890, with visible light output may be provided to indicate status such as battery replacement thereby providing an example indication of battery life.

Figure 9:
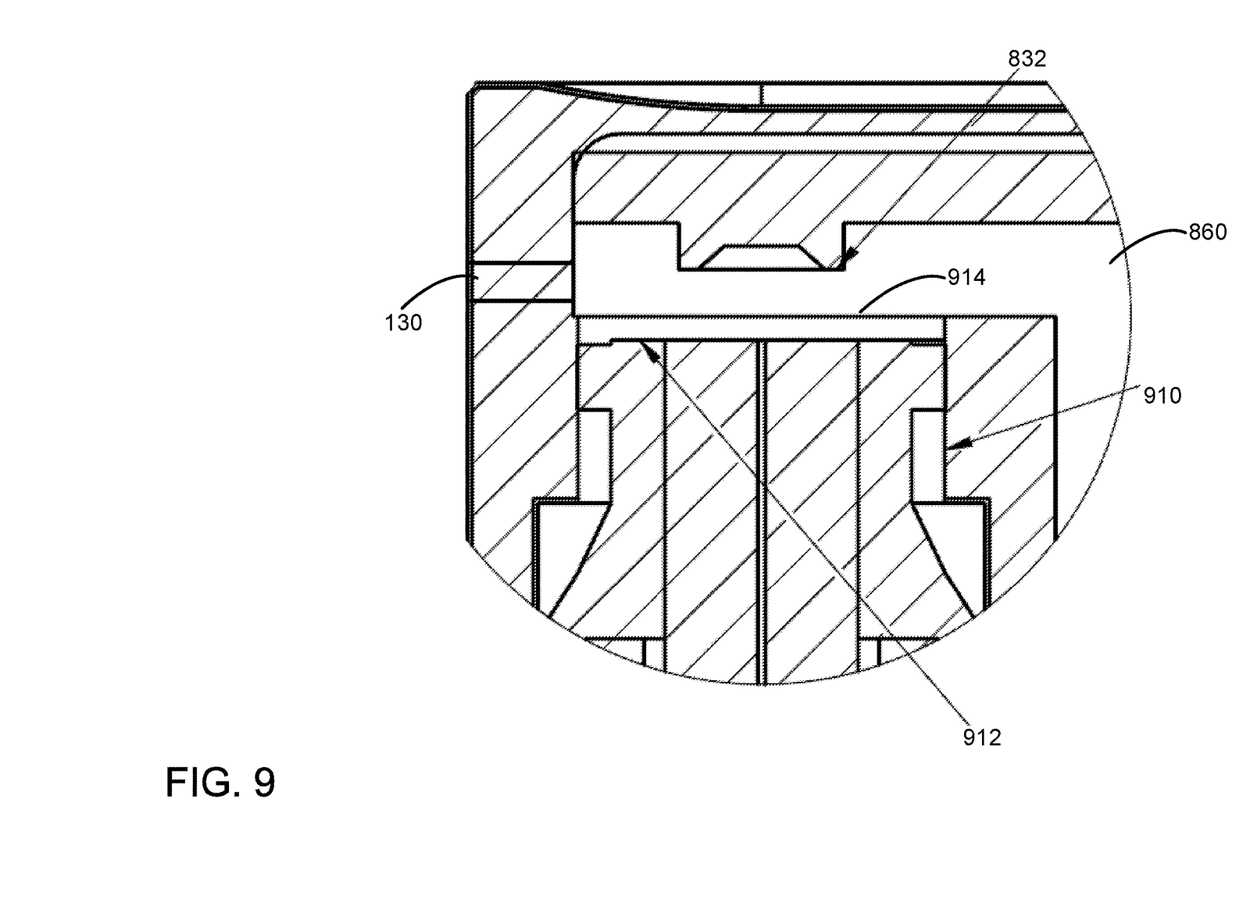

FIG. 9 shows an enlarged portion of FIG. 8. For example, the figure illustrates threaded luer portion 910 of the receiving portion that can locate and fix the port in one example. The LED 832 is also shown positioned such that it is aligned with a central axis of aperture 120. Although a single LED is shown, multiple LEDs may be configured to project into aperture 120 when the injection port is locked into position.

As illustrated, a flush top surface 912 of the injection port may be disposed at a selected distance spaced away from the LED and below window 130. A light channel may be formed between the LED and the top surface 912. In some examples, the light channel may be an air space. In other examples, focusing optics or transmission optics may be positioned in the light channel. In one example, empty space may extend between LED and the outside wall 914 forming an air gap space between the LED and the top surface.

Generally, in operation, a needle-free injection port is positioned through hole 150 of tether 112. The needle-free injection port is secured in place where the top portion of the needle-free injection port is disposed inside aperture 120 in a sterilization position. A locking mechanism, such as the receiving threads may secure the port in the sterilization position. In some examples, a stop may be provided to prevent insertion of the port in the aperture beyond the sterilization position, thereby preventing the port from being inserted too far into the aperture where it may damage the LED or other structure. Once in the sterilization position, operation of the UV LED may commence such that UV light is directed at the injection port for sterilization. Operation of the UV LED may require one or more switches to be activated. The switches may be engaged based on position of the port, user-buttons, etc. In some examples, an indicator may provide a signal, such as a visible light signal through the use of window 130, to a user indicating operation of the UV LED.

Figure 10:
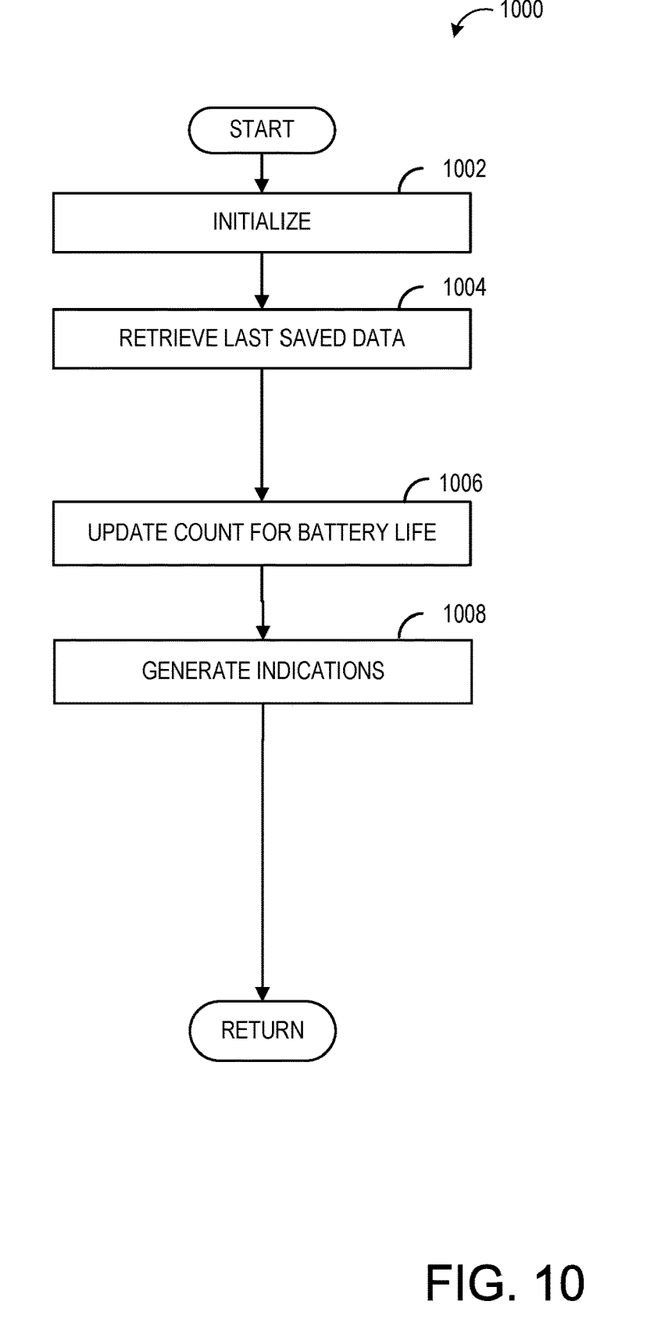
FIG. 10 shows an example routine carried out by the device.
Figure 11:
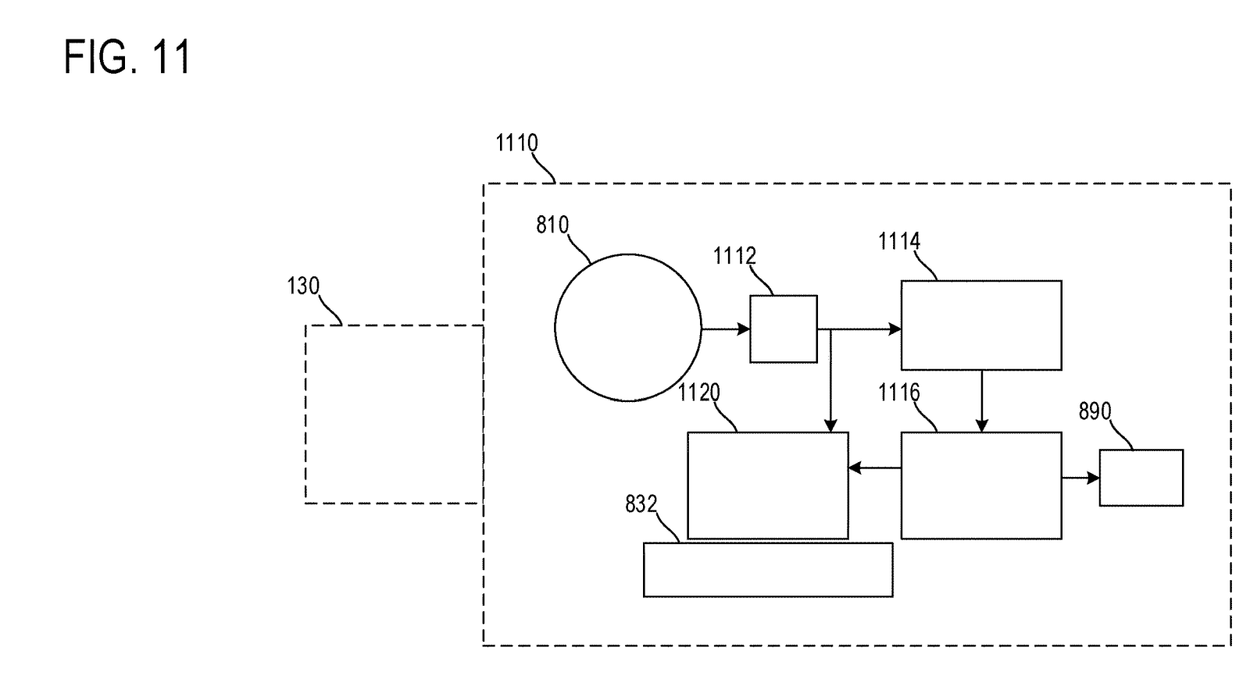
FIG. 11 shows an example diagram of an electronic control system that may be included in the device of FIGS. 1-9.

FIG. 10 illustrates an example routine that may be stored as instructions in the control system of the device, such as in the microprocessor of FIG. 11 and described in more detailed herein. For example, instructions for carrying out method 1000 and the rest of the methods included herein may be executed by a controller based on instructions stored on a memory of the controller and in conjunction with signals received from sensors and/or signals sent to actuators of the device.

The routine may include, in some examples, one or more of the illustrated steps. In one example, the method may include initializing the device at 1002, retrieving previously saved data, such as battery life, hours of LED operation, number of cycles, etc. at 1004. Then, at 1006 the routine may include updating the battery life count estimate based on current operation, and then, at 1008, generating indications based on sensed and estimated data.

In one example, the initialization may include reading whether limit switches are activated, such as the various limit switches described herein. In one example, only if multiple (e.g., two or more) limit switches are each engaged (e.g., by proper insertion of the port) is the UV LED enabled and then energized. In this example, if only one switch is engaged, but not another, an error determination may be made by the processor and an indication generated at 1008, for example lighting a malfunction light, storing an error code in memory, and/or communicating with an external device determination of the degradation, e.g., via wireless or other communication.

Note that the control system may receive signals from the various sensors of the device and may employ various actuators of the device to adjust operation based on the received signals and/or internally generated data. Further, the control system may adjust operation of the device based on instructions stored on a memory of the controller. For example, the instructions may control activation, power, deactivation, operation, etc. of the UV light source responsive to a calculated duration, measured battery voltage, etc. as described herein.

Turning now to FIG. 11, an example diagram of an electronic control system is illustrated for the device shown in FIG. 1-9. FIG. 11 illustrates a system 1110 having batteries 810 coupled with two interlocking switches. One or more batteries may be used to power the system. In the example, three CR2032 batteries are used.

Switches, such as interlock switches 1112 may be integrated within the system. In one example, the switches may provide double fault failsafe operation.

FIG. 11 additionally shows a DC/DC buck converter 1114, microcontroller 1116, current driver 1120. In operation, UV LED 832 may be powered by batteries 810, driven by driver 1120 and controlled by microcontroller 1116.

Also illustrated in FIG. 11 is optional window 130. As described above, the device may include a window with UV sensitive material generating visible light in a presence of UV energy. The window may be positioned adjacent the receiving aperture and may comprise fluorescing material. The window may provide visible status information on operation of the UV LED. Similarly, optional status LEDS may be included and are shown at 890. The status LED may indicate power status, on/off status, etc.

Figure 12:
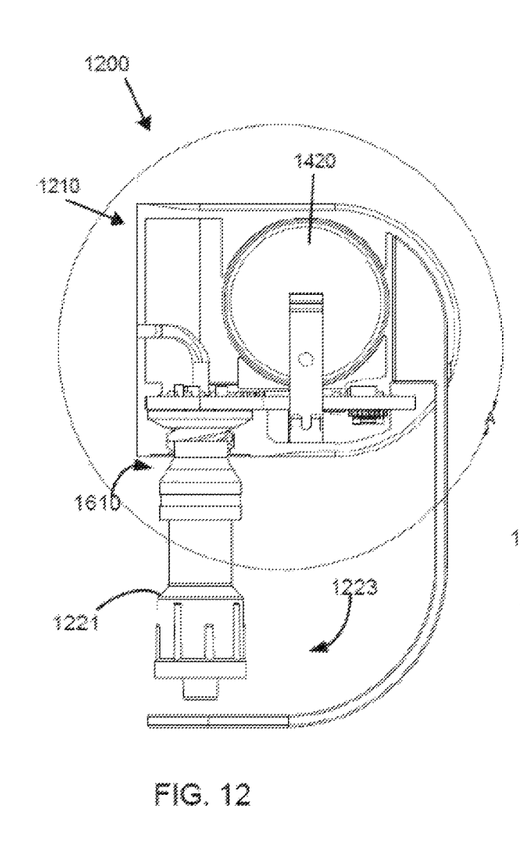
FIGS. 12-13 show another example device, and are drawn to scale, although other relative dimensions may be used, if desired. The example devices and variations thereof in these figures may also utilize the various methods described elsewhere herein, for example in FIGS. 10-11. Likewise elements from the various devices may be used in combination with elements from other example devices described herein.
Figure 13:
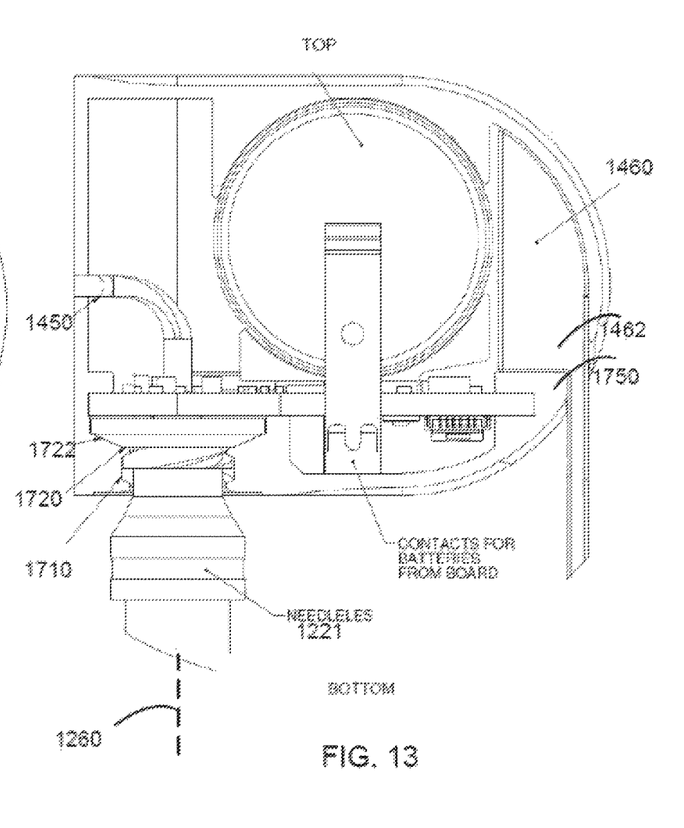

Another example device 1200 is illustrated in FIGS. 12-13. It should be appreciated that the figures herein show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example. For example, illustration of components directly coupled to one another, without any intervening components therebetween, may be distinct from components coupled together through an intermediary component. As another example, the figures may illustrate voids and spaces where there is no structural component of the device, enabling one or more components to be spaced away from one another and/or separate from one another by an unoccupied space.

In one example, the figures illustrate various components in a mechanical form illustrating relative sizing, positioning, etc. It some examples, the figures, including FIGS. 1-9 and FIGS. 12-13 may illustrate example configurations to scale, although other relative dimensioning may be used, if desired.

FIG. 12 represents a side view showing the relative positioning of the example battery pack or energy storage device 1420, also including a detail "A" shown in FIG. 13. FIG. 12 shows the device 1210 coupled with a line having a needle-free injection port (female/male luer) 1221, the top of which is to be sterilized by UV light. The port is fixed and recessed into the body by a threaded connection with the body. Additionally, a female-luer to catheter transition 1223 is shown attached to the needle-free injection port via a threaded connection and luer, also slideably coupled to the tether. The port 1221 has its male threaded section 1610 screwably engaged to mating female threads formed in the body. In one example, a threaded portion 1710 enables recessability of the needleless luer in the body and retains the port in the body during sterilization.

When fully engaged, the end of needleless luer contacts an actuation switch. For example, as illustrated, the end of needleless luer may contact an actuation ring 1720 in a concentric fashion. The actuation ring 1720 may have an open center cylinder and/or may be slideably retained to move parallel to axis 1260 by engagement of the threaded end of the needleless luer of the port. The open center enables UV radiation emitted by the UV-LED to reach the end of the port for sanitation. The actuation ring 1720 may have an angled surface 1722 that is biased against a corresponding angled surface of the body, such that the ring is biased by spring downward from the top to the bottom. The bias may be generated by loaded contactors or limit switches mounted to the board positioned between the board and the actuation ring. When the port is rotatably inserted into the body and engaged and screwed into position, its end engages the bottom surface of the actuation ring and forces the ring upward against the bias to engage the contactors and displace an element in the contractors to generate a signal, e.g., by closing a circuit.

FIGS. 12-13 also further illustrate the light pipe, or guide, 1450 to the outside of the body. Additionally, an example retaining shelf 1750 is shown for retaining the circuit board in the body. The internal walls of the body thus may include various recesses, shelves, protrusion, and other retaining features for capturing the various components as shown. Further by using the spring loaded contactors for retaining the batteries as well as coupling with the board, a simplified overall structure may be achieved, while also creating the contact-enabled insertion of the port from the opposite side of the board as compared with the batteries. Further, because each of the battery contact and port contact are on antiparallel axis, e.g., perpendicular to each other) the forces may be independent of one another to avoid losing power when inserting the port. Likewise, because the bodies' internal walls locate both the batteries and the board, as well as the luer threads, tolerance stack-up is reduced.

In some examples, the device may receive instructions from an external computing source. The external computing source may request a transmission, such as an operation condition transmission, information regarding activated duration of the UV source or status information transmission. The instructions may further provide operation instructions for controlling and powering the LED or for additional sterilization routines.

Note that the example control routines included herein can be used with various system configurations. The control methods and routines disclosed herein may be stored as executable instructions in non-transitory memory and may be carried out by the control system including the controller of the device and/or the external computing device in combination with various sensors, actuators, and other hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted.

Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

The various examples and alternative of the device described herein make it possible to better package the device in a form factor enabling convenient and effective sterilization. A technical effect achieved includes improved sterilization of access ports of a patient.

Figure 14:
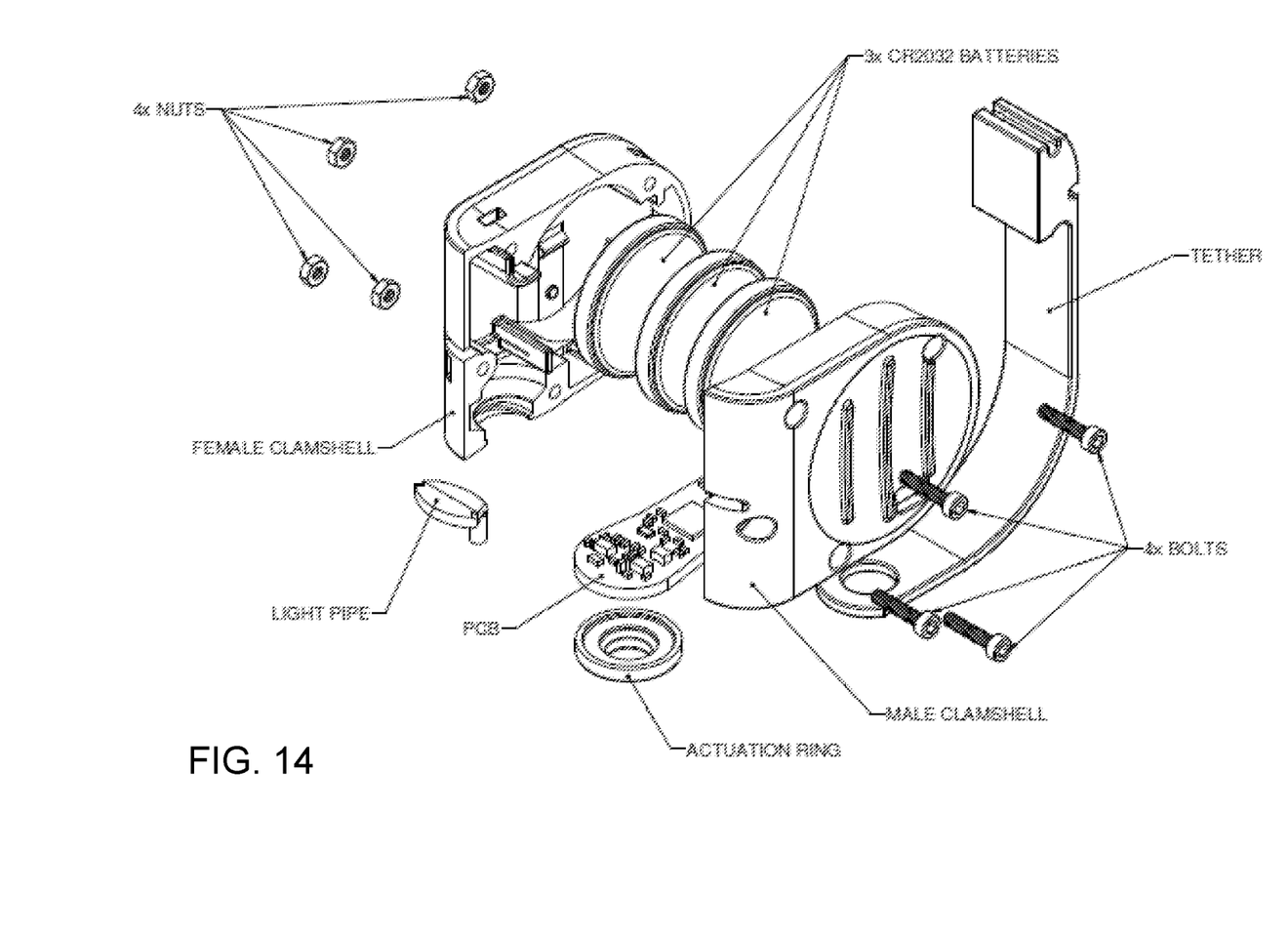
FIG. 14 shows another example device and is drawn to scale, although other relative dimensions may be used, if desired. The example device and variations thereof in this figure may also utilize the various methods described elsewhere herein. Likewise elements from the various devices may be used in combination with elements from other example devices described herein.

FIG. 14 shows an exploded view of the components of another example device, including male and female clamshell halves, for example. The example device and variations thereof in this figure may also utilize the various methods described elsewhere herein. Likewise, elements from the various devices may be used in combination with elements from other example devices described herein.

As described above, in one embodiment, a device is provided including a body with a flexible tether and a receiving aperture having a central axis. The body includes an internal cavity where the cavity houses a circular battery with a central axis perpendicular to the central axis of the aperture and a UV source positioned at an end of the receiving aperture. In some examples, the battery includes a stack of circular batteries each centrally aligned.

With the device, a method is disclosed sterilizing an access site of a patient line with the device coupled to the site. The device may include a body with a cylindrical receiving cavity having a central axis coupled to a port of the line at the site, the body forming an internal cavity housing circular battery with a central axis perpendicular to the central axis of the aperture and a UV source positioned at an end of the receiving cavity, the UV source sterilizing the port only while coupled.

As described, in some examples, the aperture being an only aperture of the body. The receiving aperture may be a receiving cavity inside the body. The aperture may be shaped and structured to receive a catheter port. For example, the aperture may be shaped and structured to receive a needleless port. In some examples, the receiving aperture may include a threaded luer portion at an end proximate to the UV source. The UV source may be positioned at an end of a cylindrical receiving portion of the aperture and opposite a circular opening of the aperture.

In some examples, the may include a body having a molded clamshell configuration with an internal wall dividing the receiving portion of the aperture from a battery cavity.

The body may have a first and second generally planar sides perpendicular to the central axis of the battery. The body may be U-shaped. For example, the body may have first and second generally planar sides perpendicular to the central axis of the batteries and is U-shaped, wherein the batteries are situated in the curved U portion and the aperture includes a cylindrical receiving portion at an opposite end of the curved U portion with a circular opening at a top end opposite the curved U portion. A circuit board may be positioned along one of the two legs of the U-shaped body and electrically coupled to the battery. In some examples, the circuit board may be positioned along a top surface of the body. In other examples, the circuit board may be positioned along a bottom surface of the body. In even other examples, the circuit board may be vertically positioned along an edge surface.

The UV source may be an LED surface mounted to a board. In some examples, the LED may be positioned along the central axis of the aperture. The device may include a circuit having interlock switches, a buck mode converter, a constant current driver, and/or a microcontroller with instructions stored thereon in non-transitory memory.

In some examples, the UV source may be activated only if the aperture is filled with a device that abuts an end stop or where a port engages one or more operation switches, such as through an actuation ring.

As another example, a device, is provided including a body having a cylindrical receiving portion forming an aperture and having a central axis. The further forming an internal cavity. The cylindrical energy storage device disposed with a central axis perpendicular to the central axis of the aperture and the body having a UV-activated window. Further, the device may include a UV source positioned at an end of the receiving portion mounted to a board within the body having a processor with instructions therein for tracking an activated duration of the UV source.

A method for controlling operation of the LED of the device via a processor coupled in the cavity and positioned on a circuit board positioned along an edge of the body is provided. In some examples, the processor is configured to carry out instructions stored in memory, where the the instructions including instructions to power the LED and track usage of the battery over operation and generate an indication of battery life.

The housing may include an operation indicator window. In the window, UV sensitive material may generate visible light in a presence of UV energy. In some examples, the window may be positioned adjacent the receiving aperture and may include fluorescing material.

As another example, a device is provided including a body with a receiving aperture having a central axis, the body forming an internal cavity, the cavity housing a battery; a UV source positioned at an end of the receiving aperture; and a mechanical self-actuator engagement receiver in the cavity electrically enabling powering of the UV source upon mechanical insertion of a port. The battery may include a circular battery with a central axis perpendicular to the central axis of the aperture. As such, in some examples, the body may have first and second generally planar sides perpendicular to the central axis of the batteries.

In some examples, a circuit board may be positioned below the battery and between the battery and the cavity. The board may be planar and elongate. The body may include molded-in shelves for retaining the circuit board.

The device may include a light pipe coupled from the UV source to an external window of the body, where a UV sensitive visible light producing material is positioned at the window. Further, the device may include an actuation ring with an open central region slideably held in the body and positioned around the UV source such that the UV source is aligned with the open central region. In some examples, an actuation ring is provided with an open central region slideably held in the body and positioned around the UV source such that the UV source is aligned with the open central region, and one or more contactors mounted to the circuit board and outside the open central region such that the contacts will be contacted and engaged upon sliding of the actuation ring upon insertion of a port to the aperture.

The device also may include a photodiode mounted to the board and positioned aligned with the open region of the actuation ring so that the photodiode can sense UV energy with a port fully inserted to the aperture.

The device may be packaged in a sterile package.

In some examples, the further device may include a wireless device to transmit communications to an external device based on sensed or calculated data by a processor in the body.

The device is further disclosed, in some examples, as having a receiving surface for a gel, such as adhesive colloid hydrogel. In some examples, one or more of the first and second generally planar sides may be prepared with and include an adhesive colloid hydrogel.

A system is further disclosed with the device and a patient base having a mechanical structure connector for receiving one or more of the device and an access site line. The site line having a port shaped to be received in the receiving portion. Similarly, a kit is disclosed including the device and a plate with adhesive gel on one side and a receptacle on an opposite side. In some examples, the receptacle shaped to releasably couple to a line of a catheter, the receptacle being optionally self-locking in one direction, and slideably coupled in an opposite direction, to the line.

The following claims particularly point out certain combinations and sub-combinations regarded as novel and nonobvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A device, comprising:
a body with a flexible tether, the flexible tether extending away from and external to the body, and a receiving aperture having a central axis, the body forming an internal cavity, the cavity housing a circular battery with a central axis perpendicular to the central axis of the aperture and offset from the central axis of the aperture;
a UV source positioned at an end of the aperture; and
a window with a UV activated material arranged in a wall of the body.

2. The device of claim 1, wherein the battery includes a stack of circular batteries each centrally aligned, and wherein the stack of batteries is spaced away from and adjacent to the aperture.

3. The device of claim 2, wherein the body has first and second generally planar sides perpendicular to the central axis of the battery, connected by a U-shaped edge wall, wherein the battery is situated in a curved U-shaped portion adacent to the aperture that includes a cylindrical receiving portion at an opposite end of the curved U-shaped portion with a circular opening at a top end opposite the curved U-shaped portion, a circuit board positioned along one of two legs of the body and electrically coupled to the battery.

4. The device of claim 3, wherein the offset positioning of the aperture relative to the battery reduces overall outside dimensions of the device.

5. The device of claim 1, wherein an interior of the body forming the aperture is shaped and structured to receive a catheter port, and an exterior of the body, surrounding the aperture, includes opposing parallel planar walls.

6. The device of claim 1, wherein the UV source is an LED surface mounted to a board, the LED surface positioned along the central axis of the aperture and spaced away from an abutment that extends across and encloses the aperture within an interior of the body.

7. The device of claim 1, wherein the UV activated window is formed from a UV sensitive material generating visible light in a presence of UV energy, the window positioned adjacent the aperture and comprising fluorescing material.

8. The device of claim 7, wherein the UV activated window indicates an operating status of the UV source.

9. The device of claim 1, wherein the body has first and second generally planar sides perpendicular to the central axis of the battery and wherein one or more of the first and second generally planar sides comprise an adhesive colloid hydrogel.

10. The device of claim 1, wherein the aperture includes a threaded luer portion at an end proximate to the UV source.

11. The device of claim 1, further comprising a circuit having interlock switches, a buck mode converter, a constant current driver, and/or a microcontroller with instructions stored thereon in non-transitory memory.

12. The device of claim 1, wherein a curved edge wall of the body is U-shaped and couples edges of a first planar side to edges of a second planar side of the body.

13. The device of claim 1, wherein the UV source is activated when a second device is inserted into the aperture that abuts an end stop upon adjusting the second device into a sterilization position.

14. The device of claim 1, wherein the aperture is shaped and structured to receive a needleless port.

15. The device of claim 1, wherein the body includes a molded clamshell having an internal wall dividing a receiving portion of the aperture from a battery cavity.

16. The device of claim 1, wherein the UV source is at an end of a cylindrical receiving portion of the aperture and opposite a circular opening of the aperture.

17. A device, comprising:
a body having a cylindrical receiving portion forming an aperture and having a central axis, the body forming an internal cavity, the cavity housing a cylindrical energy storage device with a central axis perpendicular to and offset from the central axis of the aperture, the body having a UV-activated window indicating a status of the device;
a flexible tether attached at a first end to an external wall of the body, extending away from the body and configured at a second end to be attached to a line; and
a UV source positioned at an end of the receiving portion mounted to a board within the body having a processor with instructions therein for tracking an activated duration of the UV source.

18. A method, comprising:
sterilizing an access site of a patient line with a device coupled to the site, the device having a body with a cylindrical receiving cavity having a central axis coupled to a port of the line at the site, the body forming an internal cavity housing a circular battery with a central axis perpendicular to the central axis of the receiving cavity and a UV source positioned at an end of the receiving cavity, the UV source sterilizing the port only while coupled;
attaching the device to a catheter line to be sterilized via a flexible tether extending from an external wall of the device and suspending the device from the catheter line while sterilizing; and
monitoring a status of the device as indicated by a UV activated window disposed in the external wall of the device, the UV activated window generating visible light based on activation by an LED.

19. The method of claim 18, further comprising controlling operation of the LED via a processor coupled in the internal cavity and positioned on a circuit board positioned along an edge of the body, the processor carrying out instructions stored in memory, the instructions including instructions to power the LED and track usage of the battery over operation and generate an indication of battery life.

* * * * *

UNITED STATES PATENT AND TRADEMARK OFFICE
CERTIFICATE OF CORRECTION

PATENT NO. : 10,195,299 B2  Page 1 of 1
APPLICATION NO. : 15/265698
DATED : February 5, 2019
INVENTOR(S) : Baker et al.

It is certified that error appears in the above-identified patent and that said Letters Patent is hereby corrected as shown below:

On the Title Page

At Item (72), Inventors:
At Line 7 after (CA) add, Michael Hutchens, Portland, OR (US)

Signed and Sealed this
Fifteenth Day of December, 2020

Andrei Iancu
*Director of the United States Patent and Trademark Office*